United States Patent
Yi et al.

(10) Patent No.: US 12,122,043 B2
(45) Date of Patent: Oct. 22, 2024

(54) FLEXIBLE MECHANISM

(71) Applicant: INDUSTRY-UNIVERSITY COOPERATION FOUNDATION HANYANG UNIVERSITY ERICA CAMPUS, Ansan-si (KR)

(72) Inventors: Byung-Ju Yi, Bucheon-si (KR); Hwantaek Ryu, Ansan-si (KR)

(73) Assignee: INDUSTRY-UNIVERSITY COOPERATION FOUNDATION HANYANG UNIVERSITY ERICA CAMPUS, Ansan-si (KR)

( * ) Notice: Subject to any disclaimer, the term of this patent is extended or adjusted under 35 U.S.C. 154(b) by 912 days.

(21) Appl. No.: 17/184,748

(22) Filed: Feb. 25, 2021

(65) Prior Publication Data

US 2021/0178610 A1 Jun. 17, 2021

Related U.S. Application Data

(63) Continuation of application No. PCT/KR2019/011121, filed on Aug. 30, 2019.

(30) Foreign Application Priority Data

Aug. 31, 2018 (KR) .......................... 10-2018-0103351
Aug. 29, 2019 (KR) .......................... 10-2019-0106386

(51) Int. Cl.
*B25J 15/12* (2006.01)
*B25J 9/10* (2006.01)

(52) U.S. Cl.
CPC ............. *B25J 15/12* (2013.01); *B25J 9/1045* (2013.01)

(58) Field of Classification Search
CPC ... B25J 15/12; B25J 9/1045; A61B 2034/301; A61B 2034/303; A61B 34/71;
(Continued)

(56) References Cited

U.S. PATENT DOCUMENTS

| 2002/0087048 A1* | 7/2002 | Brock | ........................ | B25J 3/04 |
| | | | | 600/114 |
| 2003/0135204 A1* | 7/2003 | Lee | ........................ | B25J 9/104 |
| | | | | 606/1 |

(Continued)

FOREIGN PATENT DOCUMENTS

| JP | 2017-024117 A | 2/2017 |
| JP | 2018-500054 A | 1/2018 |

(Continued)

OTHER PUBLICATIONS

International Search Report for PCT/KR2019/011121 dated Dec. 6, 2019 (PCT/ISA/210).

*Primary Examiner* — Stephen A Vu
(74) *Attorney, Agent, or Firm* — Sughrue Mion, PLLC

(57) ABSTRACT

Disclosed is a flexible mechanism including: a backbone extending in a lengthwise direction thereof; a first steering wire group including one or more steering wires disposed in a spiral direction of a first direction along the lengthwise direction of the backbone and configured to transfer a handling force applied to ends thereof to an end effector; and a second steering wire group including one or more steering wires disposed in a spiral direction of a second direction, which is different from the first direction, along the lengthwise direction of the backbone and configured to transfer a handling force applied to ends thereof to the end effector.

9 Claims, 20 Drawing Sheets

(58) Field of Classification Search
CPC .............. A61B 34/37; A61B 17/00234; A61B 2017/00323; A61B 2034/306
See application file for complete search history.

(56) References Cited

U.S. PATENT DOCUMENTS

| | | | |
|---|---|---|---|
| 2010/0004508 A1* | 1/2010 | Naito | A61B 34/37 600/141 |
| 2011/0009863 A1 | 1/2011 | Marczyk et al. | |
| 2016/0287346 A1 | 10/2016 | Hyodo et al. | |
| 2018/0092517 A1 | 4/2018 | Graetzel et al. | |

FOREIGN PATENT DOCUMENTS

| | | |
|---|---|---|
| JP | 6432050 B2 | 12/2018 |
| KR | 10-2006-0004581 A | 1/2006 |
| KR | 10-1828289 B1 | 2/2018 |

* cited by examiner

[Fig. 1A]
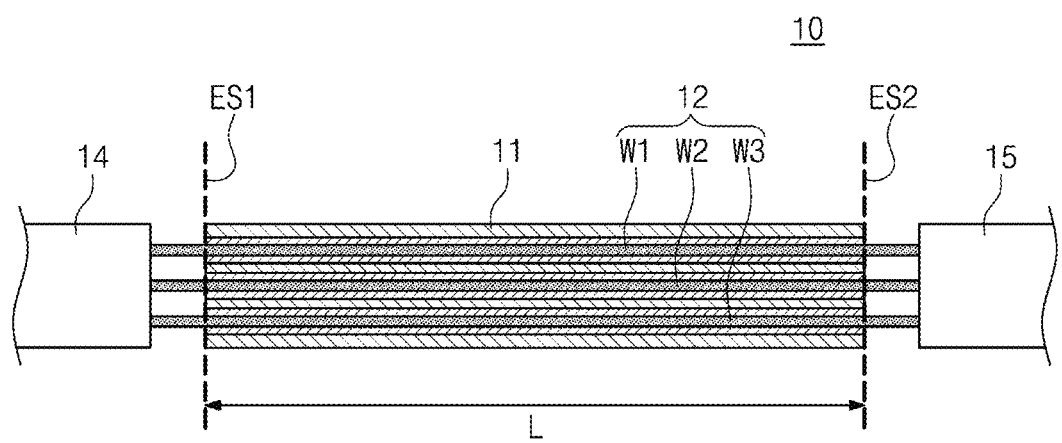

[Fig. 1B]
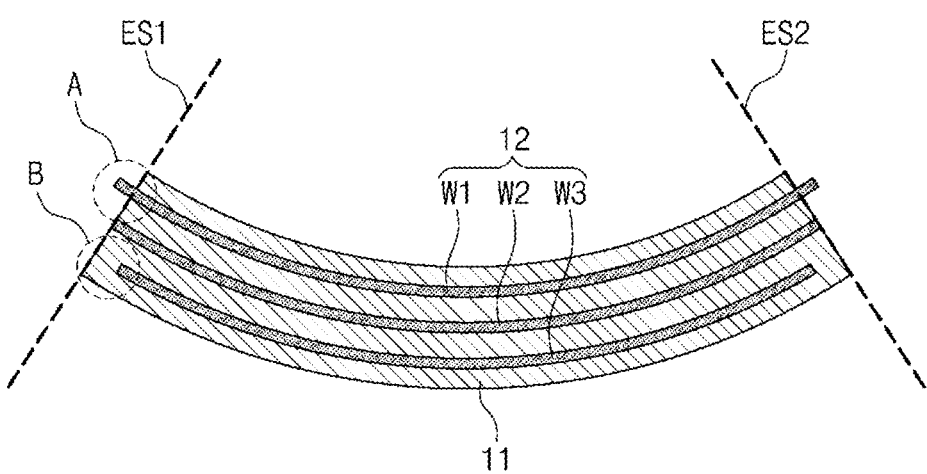

[Fig. 2]
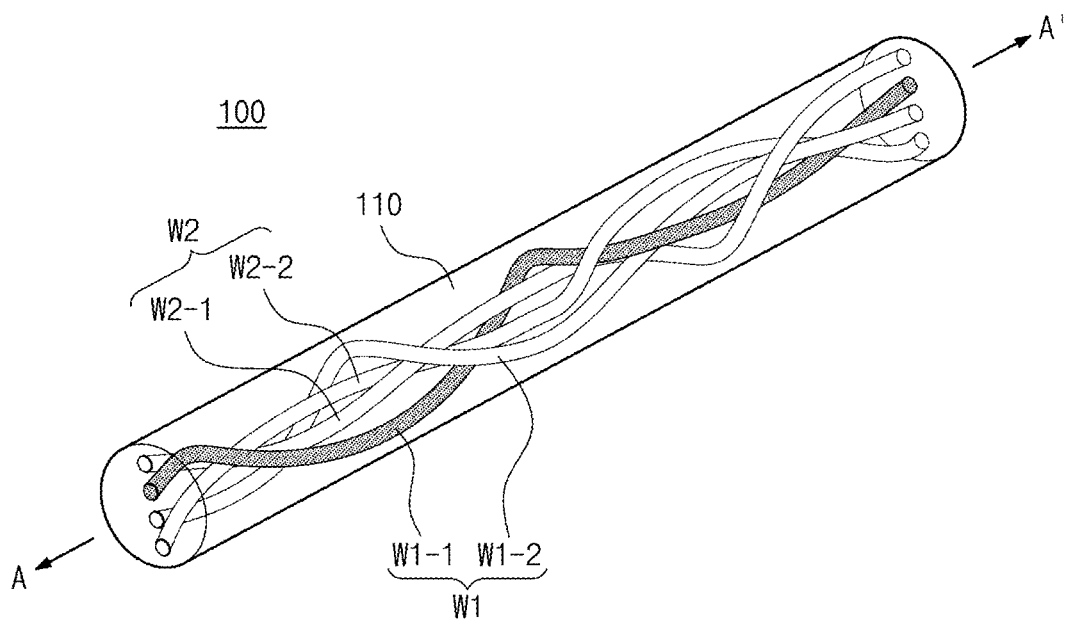

[Fig. 3A]
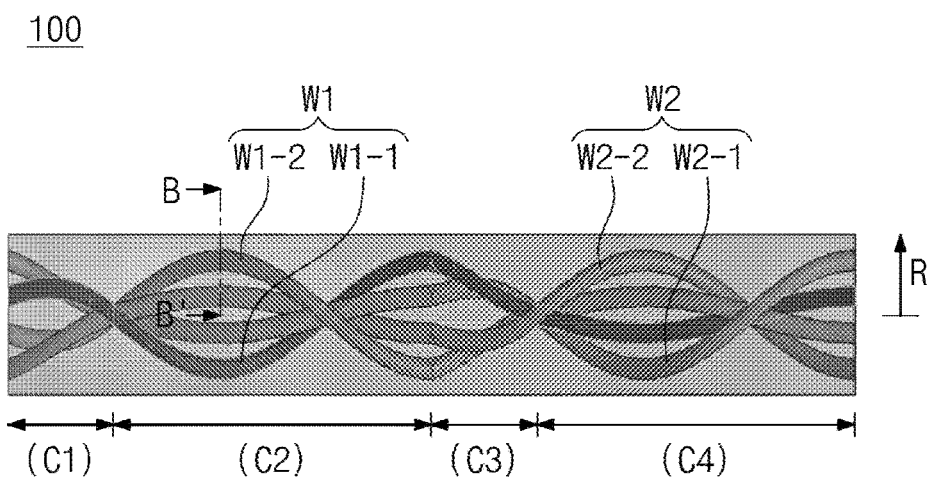

[Fig. 3B]
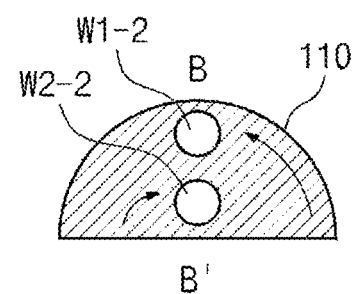

[Fig. 3C]
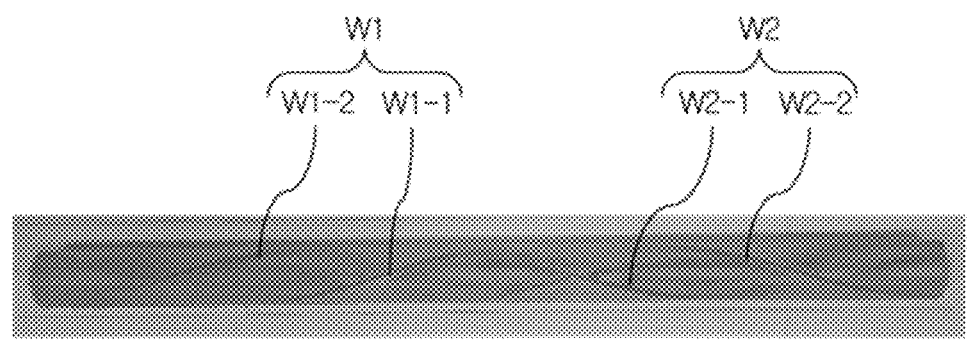

[Fig. 4B]
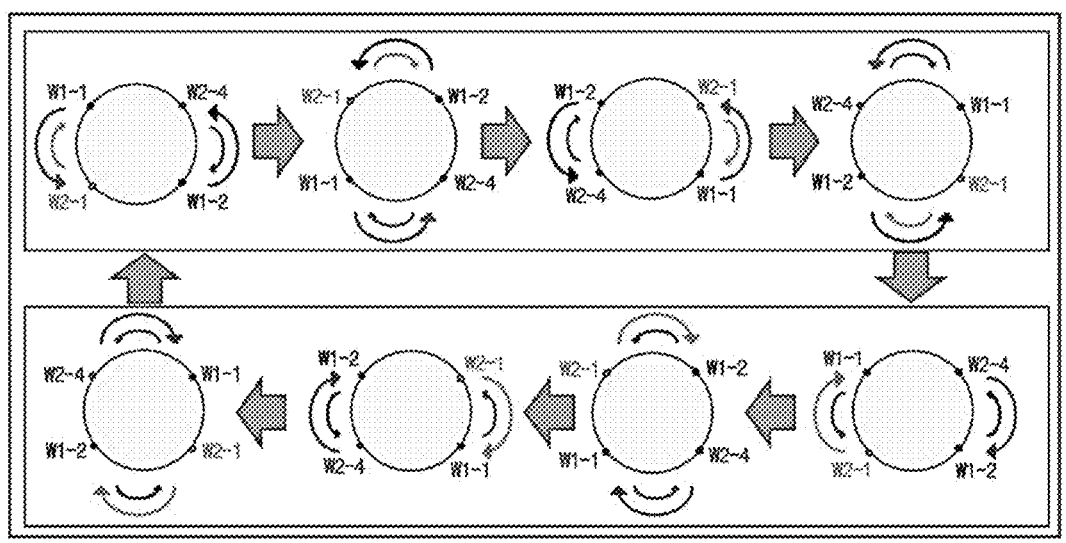

[Fig. 5A]
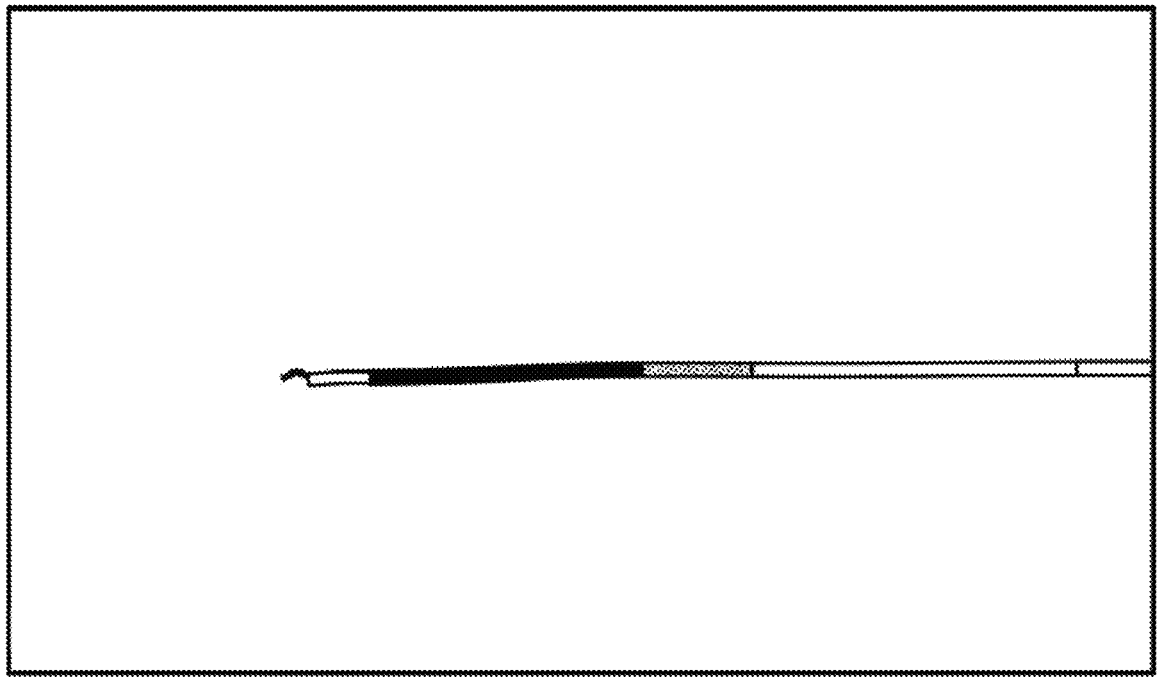

[Fig. 5B]
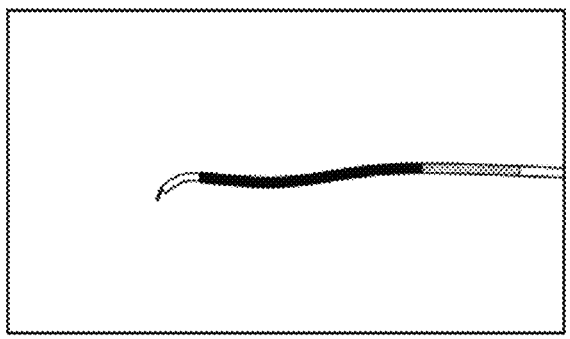
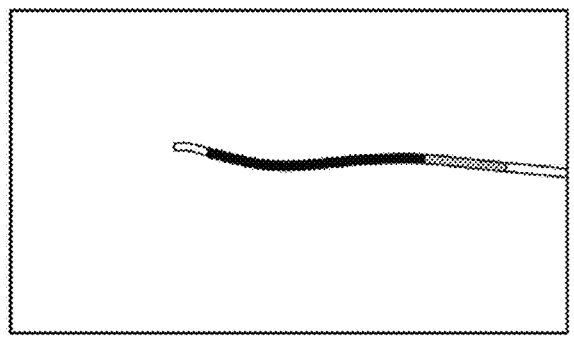
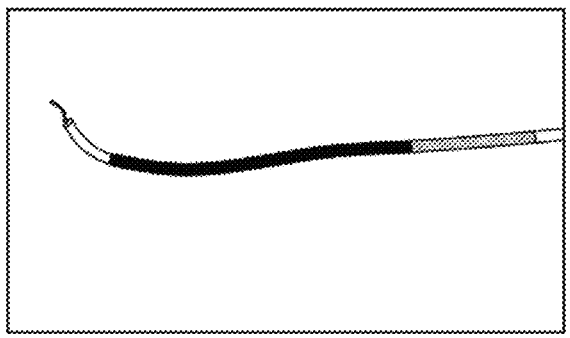
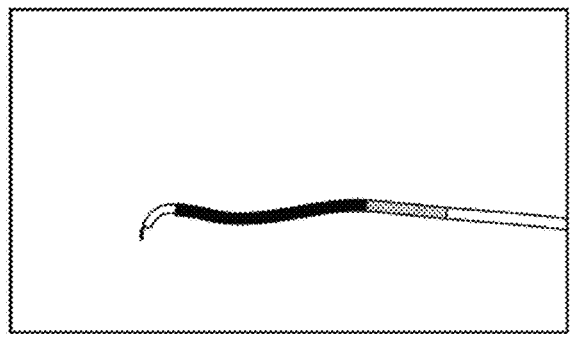

[Fig. 6A]
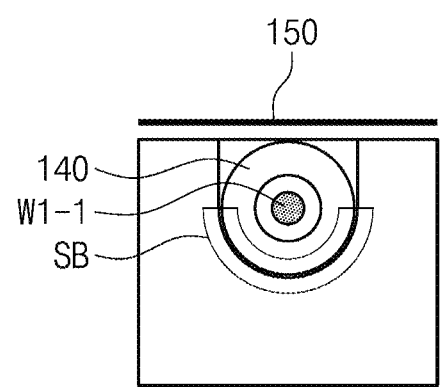

[Fig. 6B]
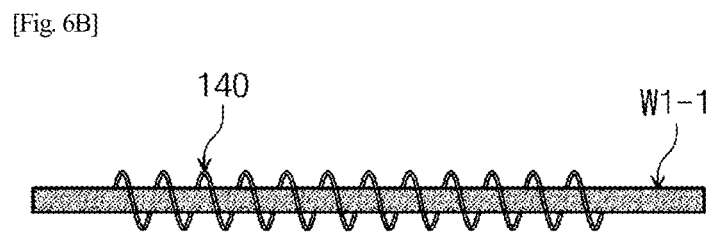

[Fig. 7]
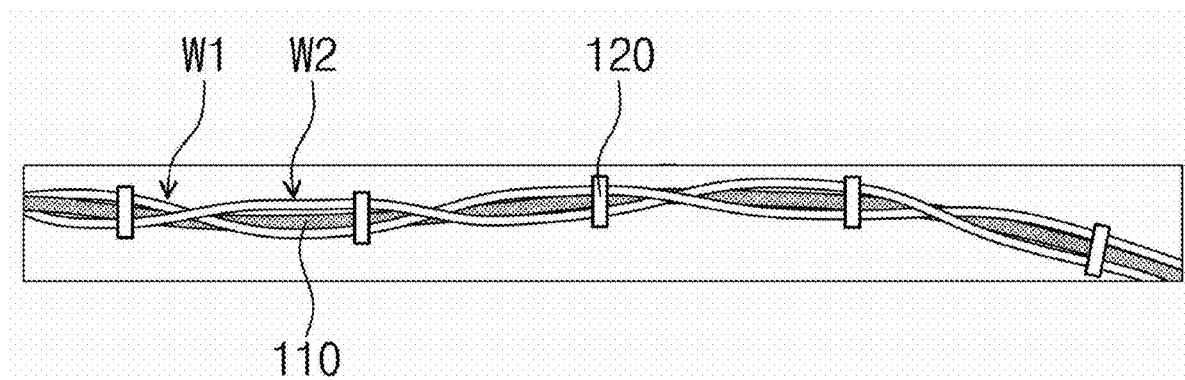

[Fig. 8]
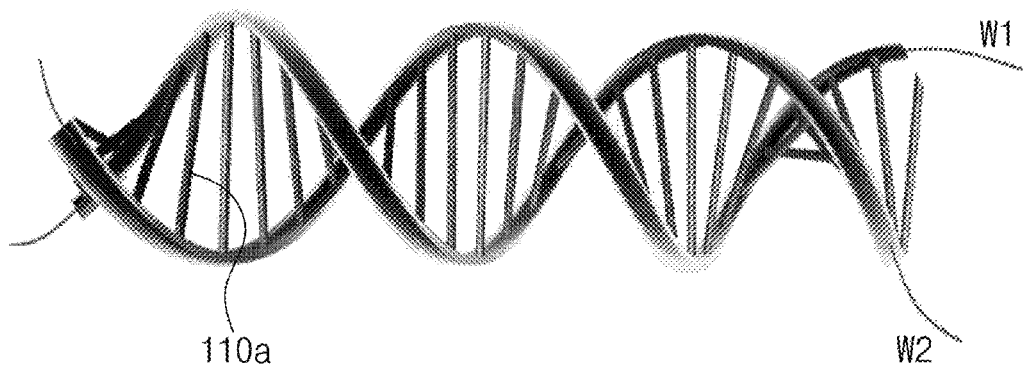

[Fig. 9]
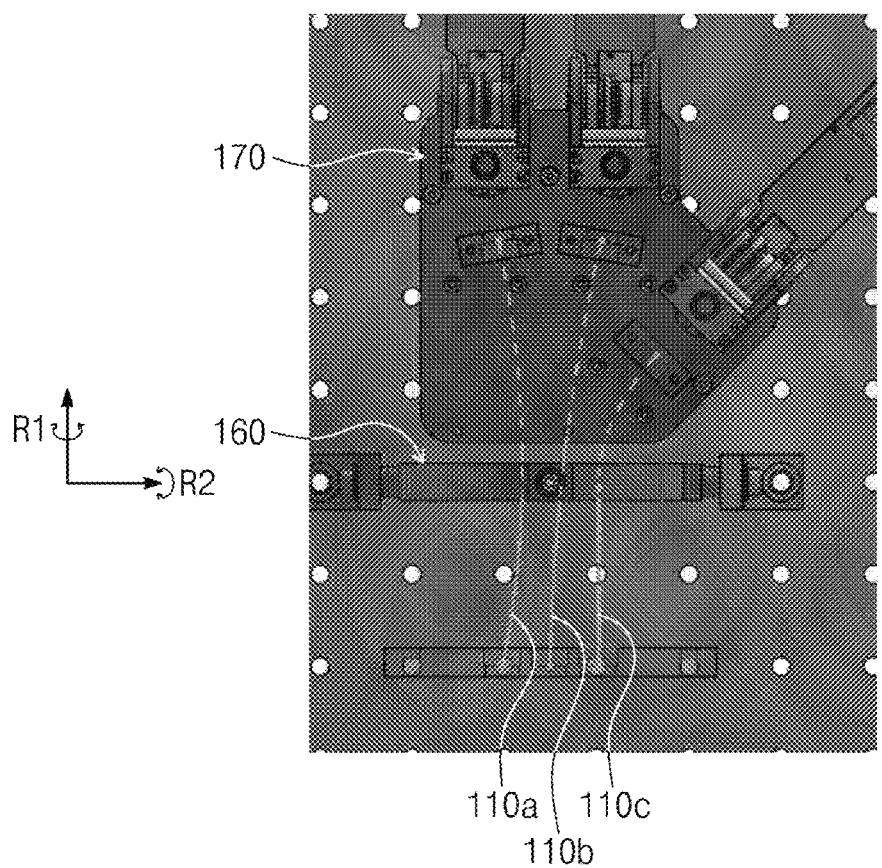

[Fig. 10]
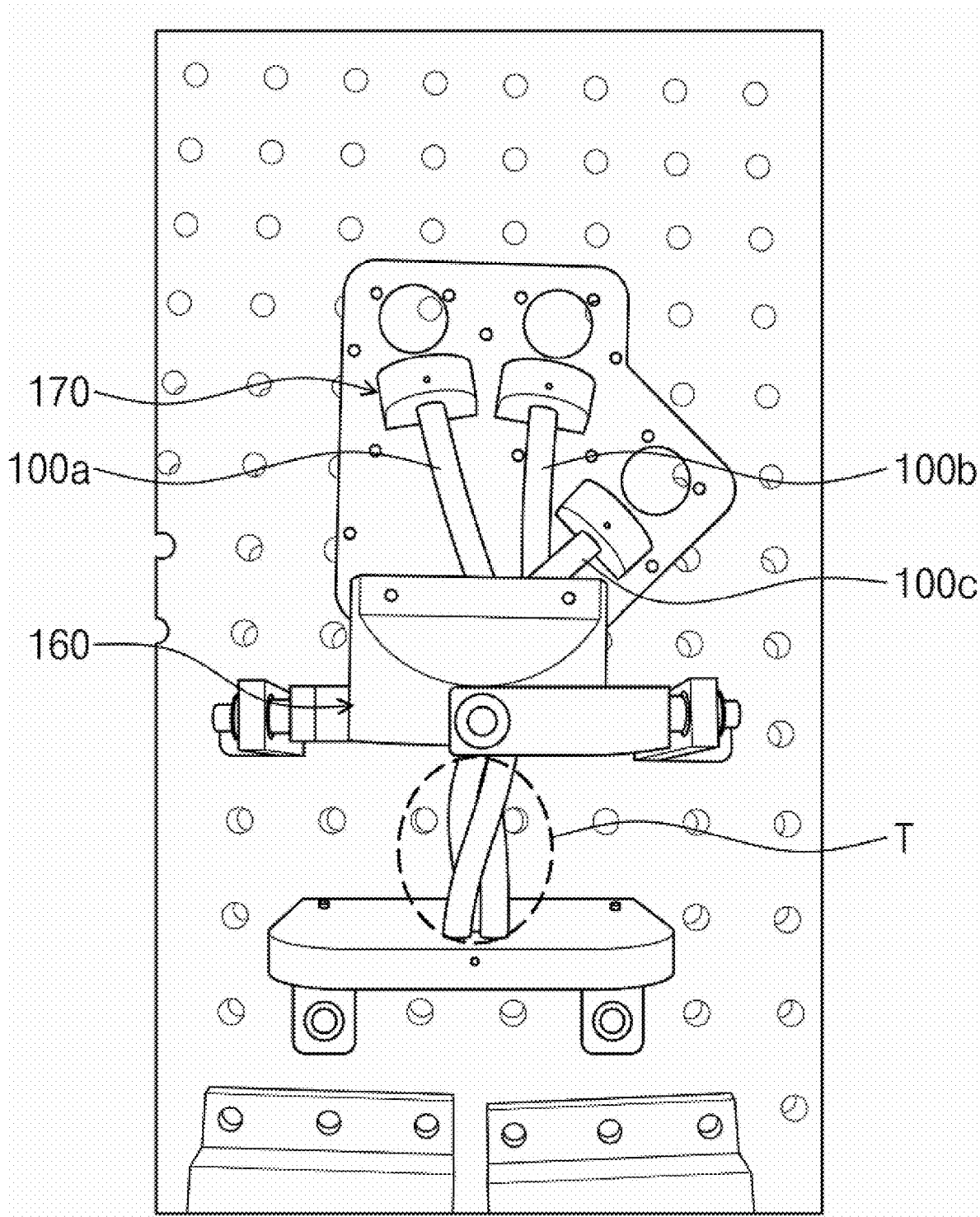

[Fig. 11A]
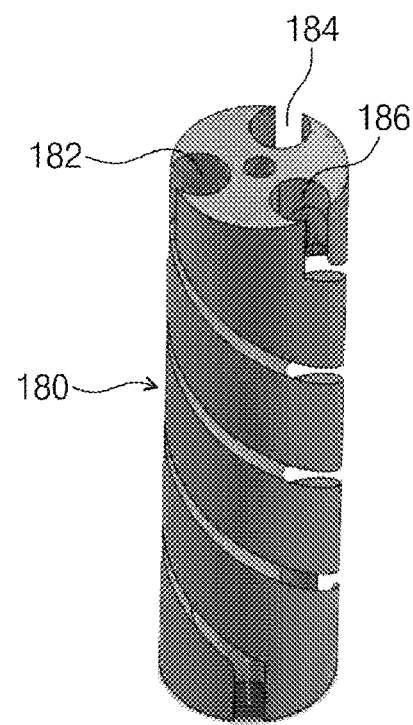

[Fig. 11B]
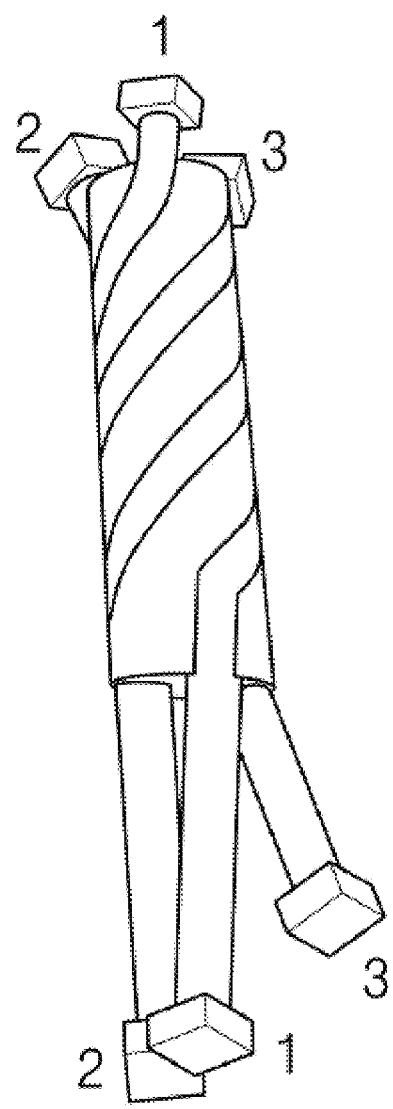

[Fig. 12]
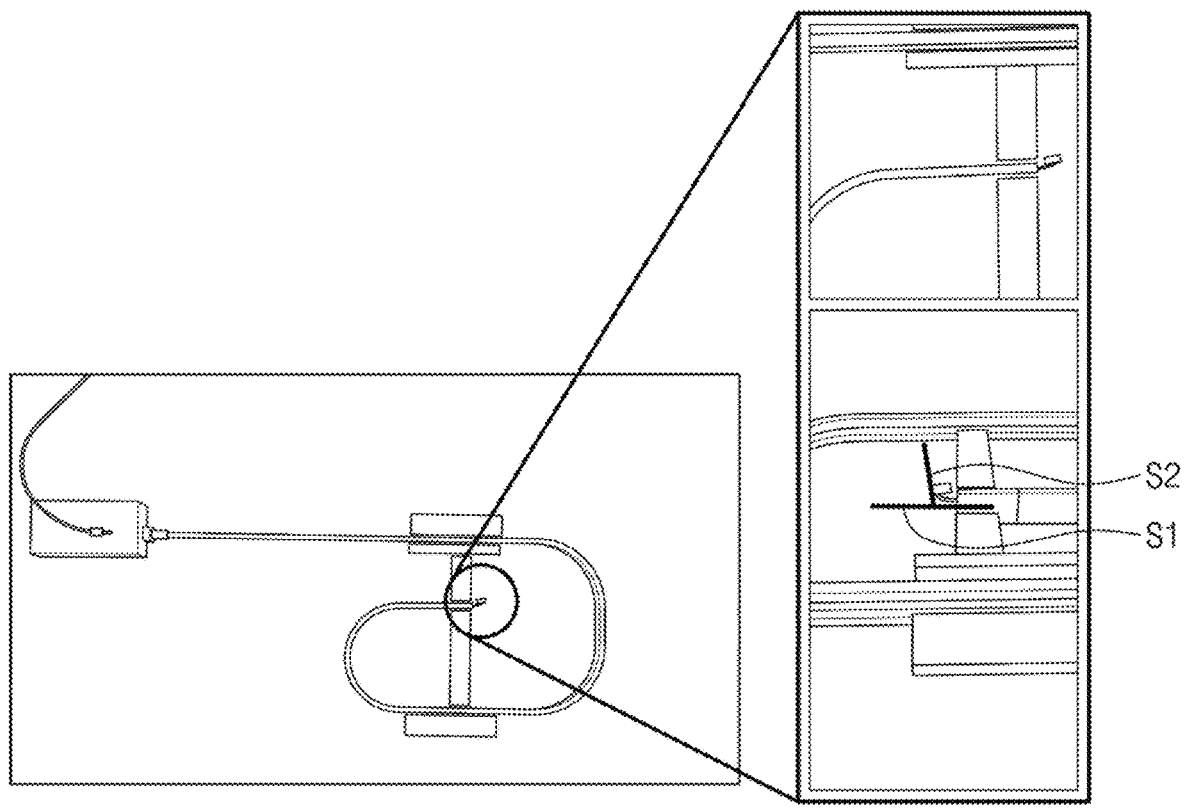

[Fig. 13]
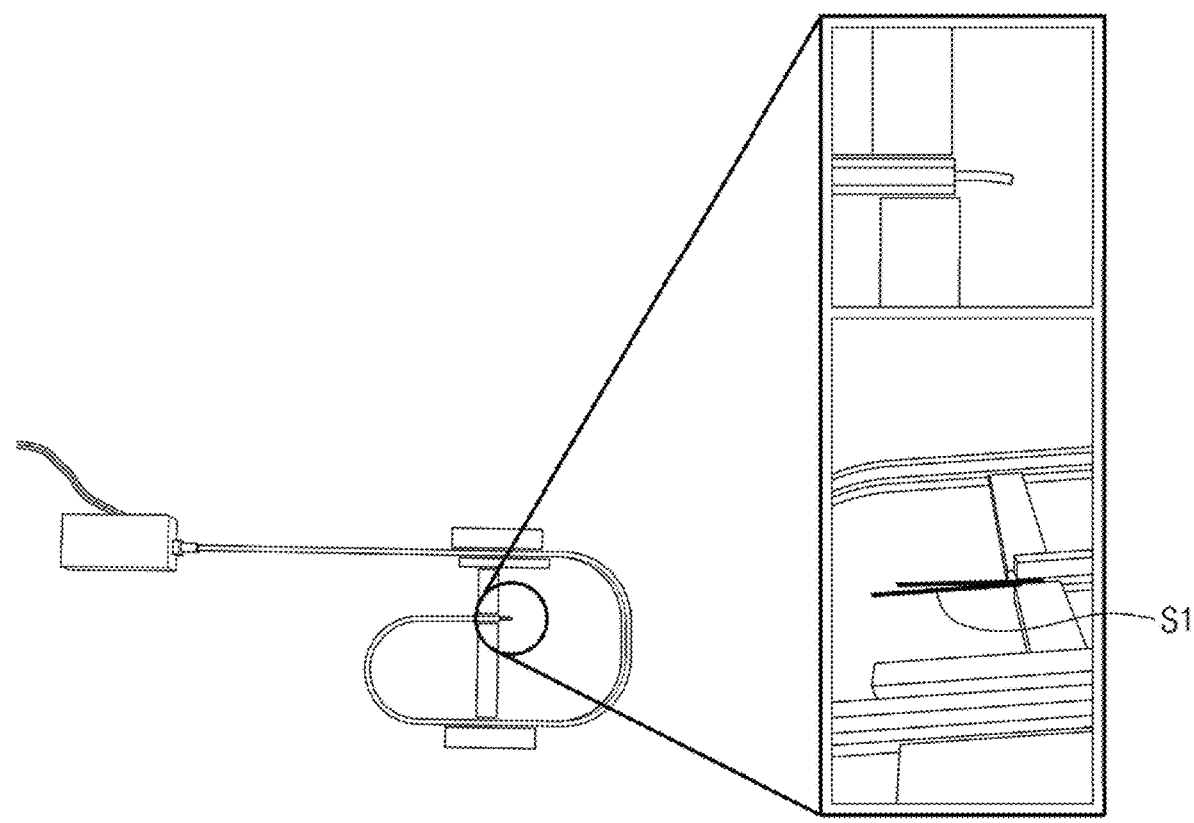

FLEXIBLE MECHANISM

BACKGROUND OF THE INVENTION

1. Field of the Invention

The present disclosure relates to a flexible mechanism, and more particularly, to a flexible mechanism that minimizes unintended control due to a deflection of an arrange route of the flexible mechanism.

2. Description of the Prior Art

The flexible mechanism may be utilized for a medical purpose for observing or treating a narrow space having curves or for a robot for controlling an end effector of a robot.

FIGS. 1A and 1B will be referenced to describe a flexible mechanism according to the related art in more detail.

Referring to FIG. 1A, the flexible mechanism 10 according to the related art may include a backbone 11, a plurality of steering wires 12 (W1, W2, and W3), a handler 14 functioning as a steering handling device, and an end effector 15. The backbone 11 is introduced into a predetermined route and is deflected according to the route. The steering wires 12 are disposed along the backbone 11, and a handling force provided by the handler 14 is transferred to the end effector 15.

In this way, when the handling force is transferred from the handler 14 to the end effect 15 through the steering wire 12, an unintended handling force may be caused according to the posture of the backbone, that is, the deflection of the route, along which the backbone passes.

For a more detailed description, referring to FIG. 1A, when the flexible backbone 11 has a linear form, a distance between a first cross-section ES1 and a second cross-section ES2 of the flexible backbone 11 may be L. In this case, distances between the first cross-sections ES1 and the second cross-sections ES2 of the steering wires W1, W2, and W3 provided in the interior of the flexible backbone 11 may be the same as L. In this case, because the lengths of the flexible backbone 11 and the steering wires W1, W2, and W3 are the same, it may be understood that the relative displacements are 0.

Then, as illustrated in FIG. 1B, when the flexible mechanism 10 is deflected, a relative displacement between the backbone 11 and the steering wire 12 may be caused. For example, referring to area A illustrated in FIG. 1B, the first steering wire W1 protrudes while passing by a first cross-section ES1 and a second cross-section ES2. As another example, Referring to area B illustrated in FIG. 1B, the third steering wire W3 fails to reach a site between the first section ES1 and the second section ES2. In this case, because an unintended change may be caused by a tension that influences an end effector 15 by the steering wires 12, a problem of an unintended control may be caused.

SUMMARY OF THE INVENTION

A technical purpose of the present disclosure is to provide a flexible mechanism that accurately transfers a handling force of a handler to an end effector.

Another technical purpose of the present disclosure is to provide a flexible mechanism that maintains a difference between the length of a backbone and the lengths of the routes of steering wires even when the backbone is deflected.

Another technical purpose of the present disclosure is to provide a flexible mechanism that minimizes an influence on the shape of a backbone by steering wires.

Another technical purpose of the present disclosure is to provide a flexible mechanism that minimizes a friction between steering wires and a backbone.

Another technical purpose of the present disclosure is to provide a flexible mechanism that minimizes an unintended control even when a plurality of backbone branches.

The technical objects of the present disclosure are not limited to the above-described ones.

In accordance with an aspect of the present disclosure, there is provided a flexible mechanism including: a backbone extending in a lengthwise direction thereof; a first steering wire group including one or more steering wires disposed in a spiral direction of a first direction along the lengthwise direction of the backbone and configured to transfer a handling force applied to ends thereof to an end effector; and a second steering wire group including one or more steering wires disposed in a spiral direction of a second direction, which is different from the first direction, along the lengthwise direction of the backbone and configured to transfer a handling force applied to ends thereof to the end effector.

The steering wires in the first steering wire group and the steering wires in the second steering wire group may be disposed such that distances thereof from the center of the backbone in a direction toward a side surface of the backbone are different along the lengthwise direction of the backbone.

The steering wires in the first steering wire group and the steering wires in the second steering wire group may have the same cycle, and the steering wires in the first steering wire group and the steering wires in the second steering wire group may be disposed along the lengthwise direction of the backbone while the inner sides and the outer sides thereof alternate.

The first steering wire group may include a 1-1-th steering wire and a 1-2-th steering wire, the second steering wire group may include a 2-1_th steering wire and a 2-2-th steering wire, and the 1-1-th steering wires and the 1-2-th steering wires may be disposed on the outer side of the 2-1-th steering wire and the 2-2-th steering wire with respect to a radial direction of the backbone during a half of a cycle of a spiral, and may be disposed on the inner side of the 2-1-th steering wire and the 2-2-th steering wire with respect to the radial direction of the backbone during the remaining half of the cycle of the spiral.

The number of the steering wires in the first steering wire group may be an even number, the number of the steering wires in the second steering wire group also may be an even number, and the number of the steering wires in the first steering wire group and the number of the steering wires in the second steering wire group may be the same.

A spiral groove, in which the steering wires in the first steering wire group and the steering wires in the second steering wire group are disposed, may be provided on an outer surface of the backbone, and a hollow, through which the steering wires pass, may be provided in the spiral groove, and a spiral maintaining part configured to maintain spiral structures of the steering wires may be further provided.

The friction areas of the spiral maintaining part and the steering wires may be smaller than the lengthwise areas of the spiral maintaining part.

The backbone may include: a first backbone, in which the first steering wire group and the second steering wire group are provided, and a second backbone, in which the first steering wire group and the second steering wire group are provided, and the first backbone and the second backbone may be spirally twisted.

The flexible mechanism may further include a spiral rail part having a spiral rail to provide spiral routes for the first backbone and the second backbone.

The backbone may include a plurality of backbone branches extending in a direction that is normal to the lengthwise directions of the first steering wire group and the second steering wire group, and the plurality of backbone branches may be disposed to be spaced apart from each other along the lengthwise directions of the first steering wire group and the second steering wire group.

According to the embodiment of the present disclosure, an unintended tension due to a deflection of the backbone can be minimized by disposing the steering wires between the steering handling device and the end effector in a spiral structure.

According to the embodiment of the present disclosure, a phenomenon, in which the shape of the backbone is distorted when the steering wires are handled by providing the steering wires of the steering wire groups such that the steering wires have spiral directions that are opposite to each other.

According to the embodiment of the present disclosure, the steering wires of the steering wire groups may be disposed to alternate to the inner side and to the outer side such that unintended forces between the steering wires of the steering wire groups are offset.

The effects of the present disclosure are not limited to the above-described ones, and may become clearer by the following description.

BRIEF DESCRIPTION OF THE DRAWINGS

The above and other objects, features, and advantages of the present invention will be more apparent from the following detailed description taken in conjunction with the accompanying drawings, in which:

FIGS. 1A and 1B are views illustrating a flexible mechanism according to the related art;

FIGS. 2 to 5B are views illustrating a flexible mechanism according to an embodiment of the present disclosure;

FIGS. 6A and 6B are views illustrating a flexible mechanism according to a modification of the present disclosure;

FIG. 7 is a view illustrating a flexible mechanism according to another modification of the present disclosure;

FIG. 8 is a view illustrating a flexible mechanism according to another modification of the present disclosure;

FIGS. 9 to 11B are views illustrating a flexible mechanism according to another modification of the present disclosure; and FIGS. 12 and 13 illustrate an experimental result for showing the excellency of the embodiments of the present disclosure.

DETAILED DESCRIPTION OF THE EXEMPLARY EMBODIMENTS

Hereinafter, preferred embodiments of the present disclosure will be described in detail with reference to the accompanying drawings. However, the technical spirit of the present disclosure is not limited to the embodiments, but may be realized in different forms. The embodiments introduced here are provided to sufficiently deliver the spirit of the present disclosure to those skilled in the art so that the disclosed contents may become thorough and complete.

When it is mentioned in the specification that one element is on another element, it means that the first element may be directly formed on the second element or a third element may be interposed between the first element and the second element. Further, in the drawings, the shapes and the sizes of the areas are exaggerated for efficient description of the technical contents.

Further, in the various embodiments of the present disclosure, the terms such as first, second, and third are used to describe various elements, but the elements are not limited to the terms. The terms are used only to distinguish one element from another element. Accordingly, an element mentioned as a first element in one embodiment may be mentioned as a second element in another embodiment. The embodiments illustrated here include their complementary embodiments. Further, the term "and/or" in the specification is used to include at least one of the elements enumerated in the specification.

In the specification, the terms of a singular form may include plural forms unless otherwise specified. In the specification, the terms "including" and "having" are used to designate that the features, the numbers, the steps, the elements, or combinations thereof described in the specification are present, and may be understood that one or more other features, numbers, step, elements, or combinations thereof may be added. Further, in the specification, "connected to" is used to mean a plurality of elements are indirectly or directly connected to each other.

Further, in the following description of the present disclosure, a detailed description of known functions and configurations incorporated herein will be omitted when it may make the subject matter of the present disclosure rather unclear.

FIGS. 2 to 5B are views illustrating a flexible mechanism according to an embodiment of the present disclosure.

Referring to FIGS. 2 to 5B, a flexible mechanism 100 according to an embodiment of the present disclosure may include at least one of a backbone 110, a first steering wire group W1, and a second steering wire group W2. Hereinafter, the elements will be described in detail.

The backbone 110 may perform a function of providing a predetermined route. For example, when the flexible mechanism 100 is used for a medical purpose, the backbone 110 may move along a route (e.g., a large intestine, a throat, or the like) in a human body. Then, the backbone 110 may be formed of a flexible material to be curved along a defection in the human body. It is apparent that the backbone 110 is formed of a human body-friendly material because it moves in the route in the interior of the body. As another example, even when the flexible mechanism 100 is used for a robot, it may be formed of a flexible material.

Steering wires W1 and W2 that connect an end effector and a steering handling device may be disposed in the backbone 110. For example, a spiral groove may be provided on an outer peripheral surface of the backbone 110 such that the steering wires W1 and W2 are disposed in the spiral groove. For example, a spiral tunnel may be provided in the interior of the backbone 110 such that the steering wires W1 and W2 are disposed in the spiral tunnel. The backbone 110 may be manufactured through various techniques such as injection-molding and 3D printing. Hereinafter, it is assumed for convenience of description that a spiral tunnel, in which the steering wires W1 and W2 are disposed, is provided in the interior of the backbone 110.

The backbone 110 may have various shapes. For example, as illustrated, the backbone 110 may have a cylindrical shape that extends in a lengthwise direction A-A' of FIG. 2. Another example will be described with reference to FIG. 7.

The first steering wire group W1 may include one or more steering wires. According to an example, the first steering wire group W1 may include an even number of steering wires. In FIG. 2, it is assumed for convenience of description that the first steering wire group W1 includes two steering wires of a 1-1-th steering wire W1-1 and a 1-2-th steering wire W1-2, but this is a simple example and the technical spirit of the present disclosure is not limited by the assumption.

The steering wires W1-1 and W1-2 of the first steering wire group W1 may adjust a tension according to a handling force applied to a steering handling device connected to ends thereof to transfer a driving force for controlling the end effector connected to the opposite ends thereof.

The steering wires W1-1 and W1-2 of the first steering wire group W1 may be disposed spirally along the lengthwise direction of the backbone 110. For example, the steering wires W1-1 and W1-2 of the first steering wire group W1 may be disposed in the backbone 110 at a predetermined cycle*N (N is an integer that is not less than 1).

The second steering wire group W2 may include one or more steering wires. According to an example, the second steering wire group W2 may include an even number of steering wires. In FIG. 2, it is assumed for convenience of description that the second steering wire group W2 includes two steering wires of a 2-1-th steering wire W2-1 and a 2-2-th steering wire W2-2, but this is a simple example and the technical spirit of the present disclosure is not limited by the assumption. For example, each of the steering wire groups may include two to six wires, but may include wires, the number of which is larger than six.

According to an embodiment, the first and second steering wire groups W1 and W2 may include the same number of steering wires. In the specification, it is assumed that the first and second steering wire groups W1 and W2 include steering wires of the same number of two.

The steering wires 2-1 and W2-2 of the second steering wire group W2 may also adjust a tension according to a handling force applied to a steering handling device connected to ends thereof to transfer a driving force for controlling the end effector connected to the opposite ends thereof.

The steering wires W2-1 and W2-2 of the second steering wire group W2 may be disposed spirally along the lengthwise direction of the backbone 110. For example, the steering wires W2-1 and W2-2 of the second steering wire group W2 may be disposed in the backbone 110 at a predetermined cycle*N (N is an integer that is not less than 1).

According to an embodiment, the steering wires in the first steering wire group W1 and the steering wires in the second steering wire group W2 may be disposed spirally along the lengthwise direction of the backbone 110, and may be disposed in different directions. The, the steering wires pertaining to the same wire group may be disposed spirally in the same direction.

As an example, the steering wires W1-1 and W1-2 in the first steering wire group W1 are disposed in a spiral shape that rotates counterclockwise in a direction A-A', and the steering wires W2-1 and W2-2 in the second steering wire group W2 are disposed in a spiral shape that rotates clockwise in an opposite direction.

Furthermore, the steering wires W1-1 and W1-2 in the first steering wire group W1 and the steering wires W2-1 and W2-2 in the second steering wire group W2 may be disposed such that distances thereof from the center of the backbone 110 in a direction of a side surface of the back bone 110 are different along the lengthwise direction of the backbone 110.

FIGS. 3A, 3B, 3C, 4A, and 4B will be referenced to describe the arrangement relationship of the steering wires in more detail.

Referring to FIG. 3A, the steering wires W1-1, W1-2, W2-1, and W2-2 of the first and second wire groups W1 and W2 may be disposed to be twisted spirally along the lengthwise direction of the backbone 110 during one cycle including C1, C2, C3, and C4.

Then, the steering wires W1-1, W1-2, W2-1, and W2-2 of the first and second wire groups W1 and W2 may have the same cycle and the shape phase in the same cycle. That is, the joints and stems of the steering wires W1-1, W1-2, W2-1, and W2-2 may be the same.

The steering wires W1-1 and W1-2 of the first steering wire group W1 and the steering wires W2-1 and W2-2 in the second steering wire group W2 may be disposed to be spaced apart from the radial center of the backbone 110 in the direction of R, and may be disposed while alternating to the inner side and to the outer side. For example, the steering wires W1-1 and W1-2 of the first wire group W1 may be disposed on the outer side of the steering wires W2-1 and W2-2 of the second wire group W2 during a half of the cycle of the spiral, and may be disposed on the inner side thereof during the remaining half of the cycle.

That is, as illustrated in FIG. 3A, in cycle C2, the steering wires W1-1 and W1-2 of the first wire group W1 may be disposed on the outer side of the steering wires W2-1 and W2-2 of the second wire group W2 with respect to the radial center of the backbone 110.

In cycle C4, in contrast with cycle C2, the steering wires W2-1 and W2-2 of the second wire group W2 may be disposed on the outer side of the steering wires W1-1 and W1-2 of the first wire group W1 with respect to the radial center of the backbone 110 Cycles C1 and C3 are sections in which the wires disposed on the outside are disposed in the inner side and the wires disposed on the inner side are disposed on the outer side.

In this way, the steering wires W1-1 and W1-2 of the first wire group W1 and the steering wires W2-1 and W2-2 of the second wire group W2 may have shapes that are twisted spirally while alternating and switching to the outer side and to the inner side.

Furthermore, the steering wires W1-1 and W1-2 of the first steering wire group W1 and the steering wires W2-1 and W2-2 in the second steering wire group W2 may be disposed in spiral directions of different directions in all cycles. For example, referring to FIG. 3B illustrating section B-B' of FIG. 3A, the spiral direction of the wire W1-2 of the first wire group W1 is a counterclockwise direction and the spiral direction of the second wire group W2 is a clockwise direction. FIG. 3C illustrates an actually implemented example.

Now referring to FIG. 4A, it can be identified how the steering wires are disposed in the planar direction of the backbone 110. As illustrated in FIG. 4A, the steering wires W1-1 and W1-2 of the first wire group W1 have the same spiral direction, the steering wires W2-1 and W2-2 of the second wire group W2 have the same spiral direction, and their spiral directions are opposite to each other.

Referring to FIG. 4B illustrating the sections in the cycles of FIG. 3A, the arrangement relationship of the wires may be understood more easily.

It can be identified in the four drawings at the upper side of FIG. 4B that the steering wires W1-1 and W1-2 are disposed on the outer side of the steering wires W2-1 and W2-2 through the illustration, in which the arrows indicating the spiral directions of the steering wires W1-1 and W1-2 of the first steering wire group 110 are disposed on the outer side of the arrow indicating the spiral directions of the steering wires W2-1 and W2-2 of the second wire group W2. In contrast, it can be identified in the four drawings at the lower side of FIG. 4B that the steering wires W1-1 and W1-2 are disposed on the inner side of the steering wires W2-1 and W2-2 through the illustration, in which the arrows indicating the spiral directions of the steering wires W1-1 and W1-2 of the first steering wire group 110 are disposed on the inner side of the arrow indicating the spiral directions of the steering wires W2-1 and W2-2 of the second wire group W2.

Furthermore, referring to FIG. 4B, it can be identified that the steering wires W1-1 and W1-2 of the first steering wire group 110 are spiral in the counterclockwise direction over all the entire spiral cycles and that the steering wires W2-1 and W2-2 of the second steering wire group 110 are spiral in the clockwise direction over all the entire spiral cycles (see the directions of the arrows).

Until now, the flexible mechanism 100 according to the embodiment of the present disclosure has been described.

Because the steering wires according to the embodiment of the present disclosure have shape that is twisted spirally along the backbone 110, the steering wires described with reference to FIG. 1B may unintentionally protrude from or be introduced into one end of the backbone even when the backbone 110 is defected, whereby a phenomenon, in which the end effector is unintentionally controlled, can be minimized.

In more detail, due to the structure, in which the steering wires are twisted spirally along the backbone 110, the lengths of the routes of the steering wires may be constantly maintained even when the flexible mechanism 100 is deflected. If the backbone 110 is deflected, the inner area of the backbone 110 becomes shorter than in the initial length L (see FIGS. 1A and 1B) and the outer area of the backbone 110 becomes longer than the initial length L (see FIGS. 1A and 1B). Then, because the steering wires are twisted along the backbone 110 in a spiral shape, they are influenced by all of the length changes occurring in the inner area and the outer area of the flexible backbone 110. In other words, the wire parts located in the inner area become looser, and the wire parts located in the outer area becomes tighter. Accordingly, the loosened areas of the wires and the tightened areas of the wires are offset. Accordingly, even when the flexible mechanism 100 is deflected, the lengths of the steering wires between one end ES1 (see FIGS. 1A and 1B) and an opposite end ES2 (see FIGS. 1A and 1B) of the backbone 110 can be maintained constantly. In order to obtain the effect, the cycle, at which the wires are twisted along the flexible backbone, should be a multiple of 360 degrees.

Furthermore, the steering wires W1-1 and W1-2 of the first steering wire group W1 and the steering wires W2-1 and W2-2 in the second steering wire group W2 may be disposed in spiral directions of different directions.

Unlike this, it can be identified that there is no problem in the initial state, in which the backbone is in a straight line state as illustrated in FIG. 5A when all the steering wires are disposed in the same spiral direction but the straight line shape of the backbone cannot be maintained and is distorted as illustrated in FIG. 5B when a tension is applied to the wires of the backbone. Accordingly, it is understood that the forces, by which the steering wires disposed in the backbone 110 tend to be spread to a straight line, cause deformation of the shape of the backbone 110.

Unlike this, according to the embodiment of the present disclosure, because the steering wires of the first and second wire groups W1 and W2 are disposed in different spiral directions, the force, by which the wires of the first wire group W1 are spread out, and the force, by which the wires of the second wire groups W2 are spread out, are offset even when the tension of the steering wires increase, whereby the deformation of the shape of the backbone 110 can be minimized.

Moreover, because the steering wires of the wire groups have spiral shapes while alternating to the inner side and the outside in a radial direction that is normal to the lengthwise direction of the backbone 110, they can help solve the slag issue of the steering wires more. If the steering wires of the first wire group are located on the outer side of the steering wires of the second wire group over all the cycles of the spiral shapes unlike in the embodiment, the steering wires of the first wire group can be more influenced by the steering wires of the second wire group when the backbone 110 is deflected, so that the unintended control or the distortion problem of the backbone 110 may be caused. However, according to the embodiment, because the steering wires of the wire groups have spiral shapes while alternating to the inner side and to the outside in the radial direction that is normal to the lengthwise direction of the backbone 110, the magnitudes of the offsetting force provided by the steering wires of the steering wire groups can correspond to each other.

Hereinafter, modifications of the above-described embodiment will be described. A description of the repeated parts will be omitted otherwise described to make the differences clear.

FIGS. 6A and 6B are views illustrating a flexible mechanism according to a modification of the present disclosure.

Referring to FIGS. 6A and 6B, the above-described steering wires of the steering wire groups may be disposed in a spiral groove formed on an outer peripheral surface of the backbone 110.

Then, when the steering wires of the steering wire groups are disposed in the spiral groove, a spiral maintaining part 140 may be provided. The spiral maintaining part 140 may have a hollow, through which the steering wires pass, in the interior thereof, and may maintain the spiral structures of the steering wires in spite of the deflection of the backbone 110. According to an embodiment, the spiral maintaining part 140, as illustrated in FIG. 6B, may have a spring shape or a hollow cylindrical shape that is shorter than the backbone 110.

In more detail, the spiral maintaining part 140 may be attached (SB) to one side of the spiral groove. The steering wires may pass through the hollow of the spiral maintaining part 140 to be disposed. In this case, the steering wires may indirectly contact the backbone 110 through the spiral maintaining part 140. Then, because the areas, by which the steering wires contact the backbone, are reduced by the spiral maintaining part 140, a handling force can be smoothly transferred to the end effector through the steering wires even in any deflection state of the backbone 110.

According to an embodiment, a sleeve 150 may be provided on an outer peripheral surface of the spiral maintaining part 140.

FIG. 7 is a view illustrating a flexible mechanism according to another modification of the present disclosure.

Referring to FIG. 7, the flexible mechanism according to the modification may include a first steering wire group W1 and a second steering wire group W2, which are formed on an outer peripheral surface of the backbone 110. The elements of the first steering wire group W1 and the second steering wire group W1 may be the same as those described above.

In the modification, the first steering wire group W1 and the second steering wire group W2 may be formed on the outer peripheral surface of the backbone 110, and the flexible mechanism may further include a clamp 120 that fixes the locations of the first steering wire group W1 and the second steering wire group W2.

The clamp 120 may function to fix the wires to one side of the backbone 110, and for example, may be a nipper, or as another example, may have a through-hole, through which the wires pass. Then, the size of the hole of the through-hole may be rather small as compared with the diameter of the wires such that the wires may be fixed.

The clamp 120 may fix sides of the wires in the first steering wire group W1 and the second steering wire group W2. For example, the clamp 120 may be disposed at an inflection point, at which the joint of a wire is changed to a furrow.

FIG. 8 is a view illustrating a flexible mechanism according to another modification of the present disclosure.

Referring to FIG. 8, the backbone 110a according to the modification may include a plurality of backbone branches that extend in a direction that is normal to the lengthwise directions of the first steering wire group W1 and the second steering wire group W2, and the plurality of backbone branches may be disposed to be spaced apart from each other along the lengthwise direction of the first steering wire group W1 and the second steering wire group W2.

That is, while the backbone 110 has a cylindrical shape according to the embodiment, the backbone 110a has the plurality of branches that extend in the direction that is normal to the lengthwise directions of the first steering wire group W1 and the second steering wire group W2. The first steering wire group W1 and the second steering wire group W1, and the plurality of branches may be flexure hinge-coupled to each other. The lengths of the branches that connect the first steering wire group W1 and the second steering wire group W2 may become shorter as they go from the centers of the joints to the outside of the joints of the first steering wire group W1 and the second steering wire group W2.

Furthermore, a spiral sleeve may be provided to fix the wires of the first steering wire group W1 and the second steering wire group W2.

Meanwhile, according to another modification of the present disclosure, the spiral directions of the first steering wire group W1 and the second steering wire group W2 may be the same. That is, the spiral directions of the first steering wire group W1 and the second steering wire group W2 may be opposite or the same.

Further, according to the modification, the number of the wires having the spiral structures is not specifically limited. For example, the number of the wires may be selected from two to twelve according to a design by an ordinary person in the art. Of course, the number of the wires may be smaller than two or larger than twelve.

FIGS. 9 to 11B are views illustrating a flexible mechanism according to another modification of the present disclosure.

The modification will be described with the assumption that the flexible mechanism is applied for a robot. Furthermore, the flexible mechanism according to the modification may include a plurality of sub-flexible mechanisms. Then, as illustrated in FIG. 9, the plurality of sub-flexible mechanisms may include the flexible mechanisms according to the embodiment, which have been described above. That is, a first flexible mechanism 110a, a second flexible mechanism 110b, and a third flexible mechanism 110c may be provided. The first flexible mechanism 110a, the second flexible mechanism 110b, and the third flexible mechanism 110c may pass through a gimbal 160 that provides a degree of freedom of rotation and be connected to an end effector 170.

The gimbal 160 may provide a second degree of freedom of rotation in the direction of first and second axes R1 and R1 to the end effector 170. If the first flexible mechanism 110a, the second flexible mechanism 110b, and the third flexible mechanism 110c are disposed in parallel to each other, a deviation may be caused in the tensional states of the wires of the first flexible mechanism 110a, the second flexible mechanism 110b, and the third flexible mechanism 110c, according to the rotational state of the gimbal 160. In this case, an unintended handling force may also be caused. For example, when any one of the first flexible mechanism 110a, the second flexible mechanism 110b, and the third flexible mechanism 110c is eccentric to the center of the rotational axis of the gimbal 160, the tensions of the steering wires may become uneven unintentionally.

Accordingly, as indicated by T of FIG. 10, the backbones of the first flexible mechanism 110a, the second flexible mechanism 110b, and the third flexible mechanism 110c may pass through the gimbal 160 while being twisted spirally.

Accordingly, the tensional states of the steering wires of the first flexible mechanism 110a, the second flexible mechanism 110b, and the third flexible mechanism 110c may be maintained in spite of the rotation of the gimbal 160 by arranging the spiral twisting axes of the rotational axis of the gimbal 160, and the first flexible mechanism 110a, the second flexible mechanism 110b, and the third flexible mechanism 110c.

Further, as illustrated in FIG. 11A, a spiral rail part 180 may be provided to make the spiral twisting of the first flexible mechanism 110a, the second flexible mechanism 110b, and the third flexible mechanism 110c smooth, and the first to third spiral rails 182, 184, and 186 that provide the spiral routes of the first flexible mechanism 110a, the second flexible mechanism 110b, and the third flexible mechanism 110c may be provided in the spiral rail part 180. As illustrated in FIG. 11B, when the spiral rail part 180 is actually manufactured and the first flexible mechanism 110a (denoted by 1), the second flexible mechanism 110b (denoted by 2), and the third flexible mechanism 110c (denoted by 3) are disposed in the spiral rails, the twisting states of the first flexible mechanism 110a, the second flexible mechanism 110b, and the third flexible mechanism 110c may be maintained well. That is, the spiral rail part 180 can minimize the releasing of the spiral twisting states of the first to third flexible mechanisms due to the deflection restoring forces of the flexible backbones.

FIGS. 12 and 13 illustrate an experimental result for showing the excellency of the embodiments of the present disclosure.

First, for comparative examples, a conventional flexible mechanism including steering wires having not a spiral structure but a parallel arrangement relationship and a flexible mechanism according to the embodiment of the present disclosure were prepared.

FIG. 12 illustrates the case, in which the deflection of the backbone is arbitrarily derived by disposing a rail having a predetermined curvature in the flexible mechanism according to the related art. A steering handling device was not operated to simply identify whether unintended tensions of the steering wires according the deflection of the backbone were caused. In this case, it could be identified that one end of the backbone, at which an effector was disposed, was deflected in a direction of S2 from a reference line S1 that is the lengthwise direction of the backbone. That is, it could be identified that in the case of the steering wires disposed in parallel, an unintended tension was caused by the slag of the steering wires when the backbone was defected, and accordingly, the unintended handling force was caused in the end effector.

Unlike this, as illustrated in FIG. 13, it could be identified that there was few changes from the reference line S1 when the flexible mechanism according to the embodiment of the present disclosure was disposed in the same rail. That is, according to the embodiment, it could be identified that the tensions on the end effector by the steering wires were maintained constantly when the backbone was deflected.

Although the preferred embodiments of the present disclosure have been described in detail until now, the scope of the present disclosure is not limited to the embodiments and should be construed by the attached claims. Further, it should be understood that those skilled in the art to which the present disclosure pertains may variously correct and modify the present disclosure without departing from the scope of the present disclosure.

What is claimed is:

1. A flexible mechanism comprising:
a backbone extending in a lengthwise direction thereof;
a first steering wire group comprising one or more steering wires disposed in a spiral direction of a first direction along the lengthwise direction of the backbone and configured to transfer a handling force applied to ends thereof to an end effector; and
a second steering wire group comprising one or more steering wires disposed in a spiral direction of a second direction, which is different from the first direction, along the lengthwise direction of the backbone and configured to transfer a handling force applied to ends thereof to the end effector,
wherein a spiral groove, in which the steering wires in the first steering wire group and the steering wires in the second steering wire group are disposed, is provided on an outer surface of the backbone, and
wherein a hollow, through which the steering wires pass, is provided in the spiral groove, and a spiral maintaining part configured to maintain spiral structures of the steering wires are further provided.

2. The flexible mechanism of claim 1, wherein the steering wires in the first steering wire group and the steering wires in the second steering wire group are disposed such that distances thereof from a center of the backbone in a direction toward a side surface of the back bone are different along the lengthwise direction of the backbone.

3. The flexible mechanism of claim 2, wherein the steering wires in the first steering wire group and the steering wires in the second steering wire group have a same cycle, and
wherein the steering wires in the first steering wire group and the steering wires in the second steering wire group are disposed along the lengthwise direction of the backbone while inner sides and the outer sides thereof alternate.

4. The flexible mechanism of claim 2, wherein the first steering wire group comprises a 1-1-th steering wire and a 1-2-th steering wire,
wherein the second steering wire group comprises a 2-1-th steering wire and a 2-2-th steering wire, and
wherein the 1-1-th steering wires and the 1-2-th steering wires are disposed on an outer side of the 2-1-th steering wire and the 2-2-th steering wire with respect to a radial direction of the backbone during a half of a cycle of a spiral, and are disposed on an inner side of the 2-1-th steering wire and the 2-2-th steering wire with respect to the radial direction of the backbone during a remaining half of the cycle of the spiral.

5. The flexible mechanism of claim 2, wherein a number of the steering wires in the first steering wire group is an even number,
wherein a number of the steering wires in the second steering wire group also is an even number, and
wherein the number of the steering wires in the first steering wire group and the number of the steering wires in the second steering wire group are same.

6. The flexible mechanism of claim 1, wherein friction areas of the spiral maintaining part and the steering wires are smaller than lengthwise areas of the spiral maintaining part.

7. A flexible mechanism comprising:
a backbone extending in a lengthwise direction thereof;
a first steering wire group comprising one or more steering wires disposed in a spiral direction of a first direction along the lengthwise direction of the backbone and configured to transfer a handling force applied to ends thereof to an end effector; and
a second steering wire group comprising one or more steering wires disposed in a spiral direction of a second direction, which is different from the first direction, along the lengthwise direction of the backbone and configured to transfer a handling force applied to ends thereof to the end effector,
wherein the backbone comprises:
a first backbone, in which the first steering wire group and the second steering wire group are provided, and
a second backbone, in which the first steering wire group and the second steering wire group are provided, and
wherein the first backbone and the second backbone are spirally twisted.

8. The flexible mechanism of claim 7, further comprising:
a spiral rail part having a spiral rail to provide spiral routes for the first backbone and the second backbone.

9. A flexible mechanism comprising:
a backbone extending in a lengthwise direction thereof;
a first steering wire group comprising one or more steering wires disposed in a spiral direction of a first direction along the lengthwise direction of the backbone and configured to transfer a handling force applied to ends thereof to an end effector; and
a second steering wire group comprising one or more steering wires disposed in a spiral direction of a second direction, which is different from the first direction, along the lengthwise direction of the backbone and configured to transfer a handling force applied to ends thereof to the end effector,
wherein the backbone comprises a plurality of backbone branches extending in a direction that is normal to lengthwise directions of the first steering wire group and the second steering wire group, and
wherein the plurality of backbone branches are disposed to be spaced apart from each other along the lengthwise directions of the first steering wire group and the second steering wire group.

* * * * *